(12) United States Patent
Wang et al.

(10) Patent No.: US 11,612,303 B2
(45) Date of Patent: Mar. 28, 2023

(54) METHOD AND APPARATUS FOR LEVERAGING RESIDUE ENERGY OF CAPSULE ENDOSCOPE

(71) Applicant: CAPSOVISION Inc., Saratoga, CA (US)

(72) Inventors: Kang-Huai Wang, Saratoga, CA (US); Mark Hadley, Los Altos, CA (US); Chang-Wei Lin, Mountain View, CA (US); Kam Wing Chow, San Jose, CA (US); Hai Huynh, San Jose, CA (US)

(73) Assignee: Capso Vision Inc., Saratoga, CA (US)

( * ) Notice: Subject to any disclaimer, the term of this patent is extended or adjusted under 35 U.S.C. 154(b) by 69 days.

(21) Appl. No.: 17/383,165

(22) Filed: Jul. 22, 2021

(65) Prior Publication Data
US 2023/0021537 A1  Jan. 26, 2023

(51) Int. Cl.
*A61B 1/00* (2006.01)
*H04N 5/232* (2006.01)
*H04W 52/02* (2009.01)
*A61B 1/06* (2006.01)
*A61B 1/04* (2006.01)
*A61B 1/045* (2006.01)
*H04N 7/18* (2006.01)
*H04N 5/225* (2006.01)

(52) U.S. Cl.
CPC .......... *A61B 1/00025* (2013.01); *A61B 1/041* (2013.01); *A61B 1/045* (2013.01); *A61B 1/0684* (2013.01); *H04N 5/23245* (2013.01); *H04N 5/232411* (2018.08); *H04N 7/185* (2013.01); *H04W 52/0254* (2013.01); *H04N 2005/2255* (2013.01)

(58) Field of Classification Search
CPC ..... A61B 1/00025; A61B 1/041; A61B 1/045; A61B 1/0684; H04N 5/232411; H04N 5/23245; H04N 7/185; H04N 2005/2255; H04W 52/0254
See application file for complete search history.

(56) References Cited

U.S. PATENT DOCUMENTS

| | | | |
|---|---|---|---|
| 6,324,426 B1 | 11/2001 | Thompson | |
| 2003/0193314 A1 | 10/2003 | Solingen | |
| 2008/0045789 A1 | 2/2008 | Sawachi | |
| 2008/0147087 A1 | 6/2008 | Horn et al. | |
| 2010/0324381 A1 | 12/2010 | Glukhovsky et al. | |
| 2015/0031954 A1* | 1/2015 | Kimoto | A61B 1/00036 600/118 |
| 2022/0192467 A1* | 6/2022 | Wang | A61B 1/00016 |
| 2022/0273300 A1* | 9/2022 | Shelton, IV | H02J 50/005 |

* cited by examiner

*Primary Examiner* — Jared Walker
(74) *Attorney, Agent, or Firm* — Blairtech Solution LLC

(57) ABSTRACT

Method for leveraging battery residue energy and a capsule endoscope using the method are disclosed. The capsule endoscope is capable of performing one or more functions at a first throughput or a first peak current when the battery has sufficient energy. According to this method, whether the battery energy is sufficient is determined. Upon determining the battery energy being insufficient, at least one function of the one or more functions is performed at a second throughput lower than the first throughput, or at least one function of the one or more functions is switched to another function requiring a second peak current lower than the first peak current.

21 Claims, 3 Drawing Sheets

METHOD AND APPARATUS FOR LEVERAGING RESIDUE ENERGY OF CAPSULE ENDOSCOPE

FIELD OF THE INVENTION

The present invention relates to battery-powered capsule cameras for imaging the gastrointestinal (GI) tract. In particular, the present invention discloses methods to leverage the residue battery energy for extended functions.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot easily reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia.

An alternative in vivo image sensor that addresses many of these problems is the capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. This patent describes a capsule system using on-board storage such as semiconductor nonvolatile archival memory to store captured images. After the capsule passes from the body, it is retrieved. Capsule housing is opened and the images stored are transferred to a computer workstation for storage and analysis. For capsule images either received through wireless transmission or retrieved from on-board storage, the images will have to be displayed and examined by diagnostician to identify potential anomalies. The on-board storage capsule system does not need the wireless harness installed on the patient. Furthermore, the on-board storage capsule system requires less visits by the patient to the provider and has the benefits of streamlined workflow for both the patient and the provider.

FIG. 1 illustrates an exemplary capsule system with on-board storage, where the capsule camera is in the human gastrointestinal (GI) tract 100. The capsule system 110 includes illuminating system 12 and a camera that includes optical system 14 and image sensor 16. A semiconductor nonvolatile archival memory 20 may be provided to allow the images to be stored and later retrieved at a docking station outside the body, after the capsule is recovered. System 110 includes battery power supply 24 and an output port 26. Capsule system 110 may be propelled through the GI tract by peristalsis.

Illuminating system 12 may be implemented by LEDs. In FIG. 1, the LEDs are located adjacent to the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. Processing module 22 may be used to provide processing required for the system such as image processing and video compression. The processing module may also provide needed system control such as to control the LEDs during image capture operation. The processing module may also be responsible for other functions such as managing image capture and coordinating image retrieval.

After the capsule camera traveled through the GI tract and exits from the body, the capsule camera is retrieved and the images stored in the archival memory are read out through the output port. The received images are usually transferred to a base station for processing and for a diagnostician to examine. For capsule cameras, the entire GI examination process is powered by the internal battery. It may take more than 20 hours from the moment that the capsule camera is swallowed to the moment it is excreted from the human body. During the examination process, thousands of images will be captured, processed, and then either be stored on-board or wirelessly transmitted to an external receiver. Due to the small capsule size, the capsule device can only afford very limited power capacity. Therefore, it is very critical to utilize the battery capacity wisely in order to optimize the battery capacity usage.

For capsule endoscope application, cell batteries or button batteries are often used. There are different types of materials (i.e., chemical compositions) used for the batteries, such as alkaline, lithium and silver oxide. For each battery, there is a nominal capacity specified and the capacity is often quoted in milliamp hour (mAh). For example, an SR927 battery may have a capacity of 60 mAh at 1.2V cutoff. The battery has a nominal voltage of 1.55V and is intended for devices operated at about 1.5V. While the battery is designed to maintain relatively constant output voltage, however, the output voltage drops substantially when the battery becomes depleted. Therefore, the nominal capacity of the battery may not be fully utilized as specified. One important factor influencing the usable capacity is the battery load. In general, a load that draws a higher drain current will have lower usable capacity due to various reasons such as internal resistance, polarization effect and/or undesirable chemical reactions inside the battery.

FIG. 2 illustrates an example of battery output voltage vs. discharge capacity for two different drain currents. The drawing is intended to illustrate the nature of usable capacity or discharge capacity at different drain currents ($I_A$ and $I_B$). In FIG. 2, curves 210 and 220 correspond to the output voltage vs. discharge capacity at drain currents $I_A$ and $I_B$ respectively, where $I_A > I_B$. When the output voltage drops below a certain level (cutoff voltage 230), the battery may not be able to provide the voltage for the connected device to operate properly. As shown in FIG. 2, at a higher drain current $I_A$, the battery will deliver a lower usable capacity $Cap_A$. On the other hand, at a lower drain current $I_B$, the battery will deliver a higher usable capacity $Cap_B$.

The present invention discloses methods to leverage battery residue energy for a capsule camera without the need to retrieve the capsule.

BRIEF SUMMARY OF THE INVENTION

A method and a capsule endoscope incorporating the method are disclosed, where one or more functions are performed by the capsule endoscope at a first throughput or a first peak current when the battery has sufficient energy. According to the method, whether the battery energy is sufficient is determined. Upon determining the battery energy being insufficient, at least one function of said one or more functions is performed at a second throughput lower than the first throughput, or at least one function of said one or more functions is switched to another function, requiring a second peak current lower than the first peak current.

In one embodiment, determining whether the battery energy is sufficient corresponds to determining whether a target function has been performed for a period of time, T and whether power-on-reset is triggered; and the battery energy is determined to be insufficient if the target function has been performed for the period of time, T and the power-on-reset is triggered.

In one embodiment, determining whether the battery energy is sufficient corresponds to detecting a power voltage drop of the battery using a voltage detection circuit; and the battery energy is determined to be insufficient if the power voltage drop of the battery is over a threshold.

In one embodiment, the second peak current is determined so that (the second peak current×battery internal resistance) is sufficiently low, but said one or more functions are still operating.

In one embodiment, one or more low-voltage functions continue to operate or are activated to operate when the battery energy is insufficient; and the one or more low-voltage functions are capable of operating at a lower voltage. In one example, a voltage regulator is used to provide the lower voltage. The voltage regulator may correspond to a switching regulator.

In one embodiment, the second throughput is achieved by using a lower clock speed for the capsule endoscope. In another embodiment, the second throughput is achieved by using a lower VCC from a regulator output. In yet another embodiment, the second peak current is achieved by lower analog circuit current setting for the capsule endoscope.

In one embodiment, switching at least one function among the one or more functions to another function is achieved by turning off a power switch to turn off the at least one function among the one or more functions and to turn on the another function.

The method may further comprise detecting whether the capsule endoscope has been excreted from a human body when the battery energy is still sufficient, and enabling a wireless function at a consumer band for the capsule endoscope to transmit images stored on-board to an external device upon detecting the capsule endoscope being excreted. Detecting whether the capsule endoscope has been excreted from the human body may comprise detecting pixels of an image having substantial intensity with very low lighting or no lighting output from lighting sources of the capsule endoscope, where the image is captured using a camera of the capsule endoscope. The process of detection pixels of an image can be based on a subset of pixels less than all pixels of camera sensor array of the capsule endoscope. For example, the subset of pixels spreads across a substantial area of the camera sensor array of the capsule endoscope. A temperature sensor can also be used for detecting whether the capsule endoscope has been excreted from the human body.

In one embodiment, the external device corresponds to a specially designed wireless device or a mobile phone. The special designed wireless device or the mobile phone may further transmit the images to a PC, or LAN (Local Area Network), or to a destination through a cloud network or other internet media.

In one embodiment, said switching at least one function of said one or more functions to another function corresponds to switching a camera function to a wireless function, and wherein the capsule endoscope is switched into a wait, or sleep mode, or monitor mode prior to the wireless function if the capsule endoscope has not been excreted from a human body, where the monitor mode is used to monitor if the capsule has been excreted. The capsule endoscope can be waked up from the sleep mode and starts the wireless function upon detection of capsule excretion. For example, the capsule endoscope can be waked up from the sleep mode and starts the wireless function upon detection of capsule excretion. Furthermore, when capsule excretion is detected, the wireless function can be initiated either in active communication or by waken-up from a sleep mode by an external device.

In another embodiment, the process of switching at least one function of said one or more functions to another function corresponds to switching a camera function to an excretion detection function. The excretion detection function can be further switched to a wireless function to transmit images stored on-board upon capsule excretion detected.

DETAILED DESCRIPTION OF THE INVENTION

Figure 1:
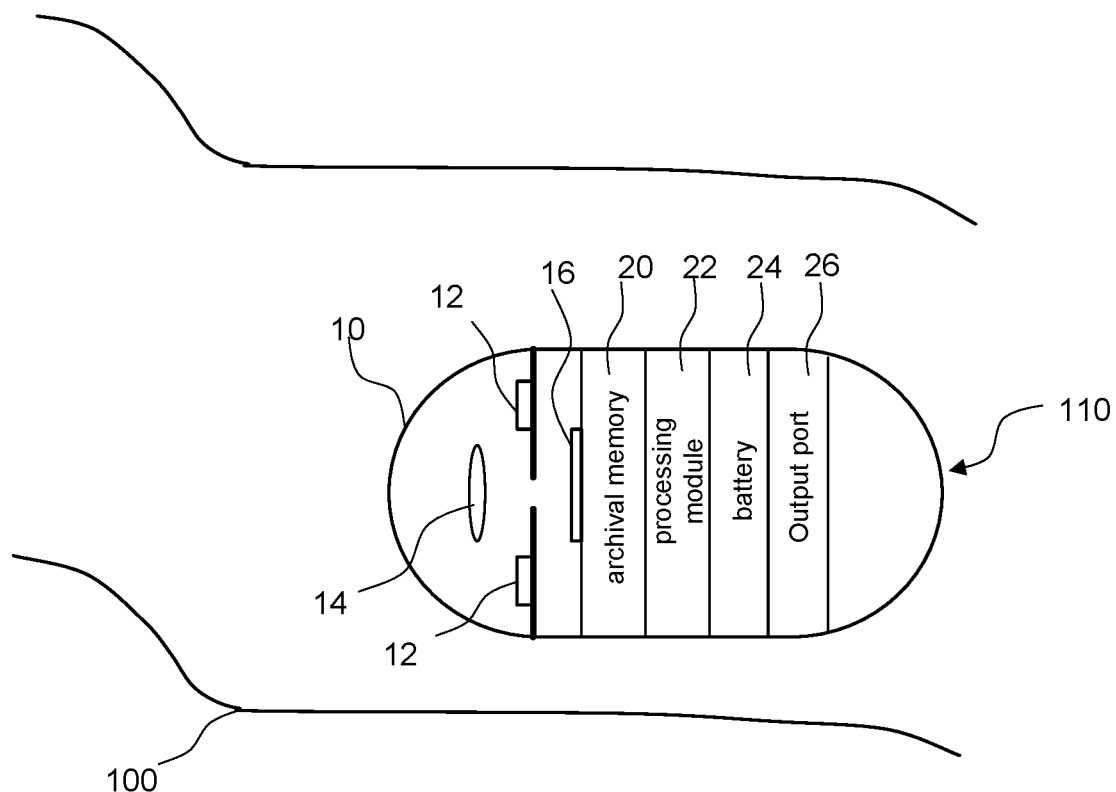
FIG. 1 illustrates an exemplary capsule system with on-board storage, where the capsule system includes illuminating system and a camera that includes optical system and image sensor.
Figure 2:
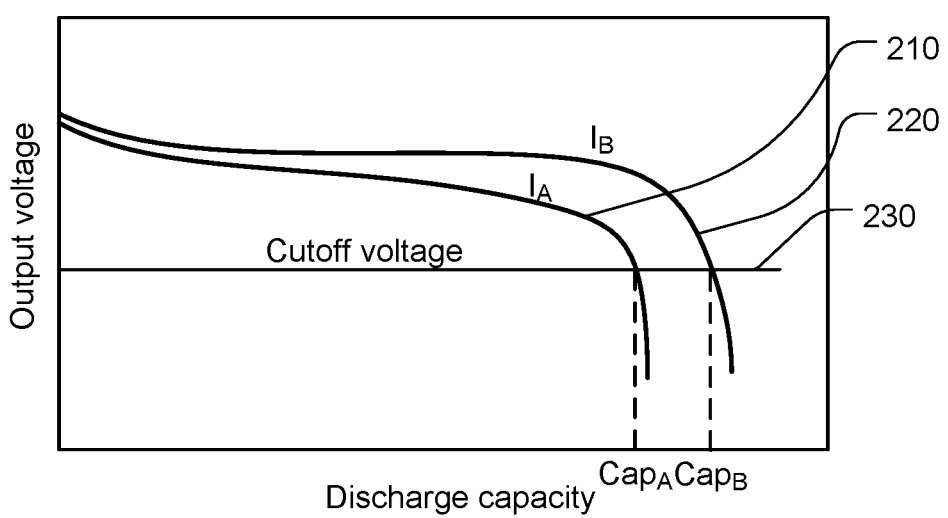
FIG. 2 illustrates an example of battery output voltage vs. discharge capacity for two different drain currents.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Endoscopes are normally inserted into the human body through a natural opening such as the mouth or anus. Therefore, endoscopes are preferred to be small sizes so as to be minimally invasive. As mentioned before, endoscopes can be used for diagnosis of human gastrointestinal (GI) tract. The captured image sequence can be viewed to identify any possible anomaly. The capsule endoscope may take more than 10 hours to travel through the human GI tract before it is excreted. During the course of travelling through the human GI tract, the capsule endoscope may have to capture tens of thousands images of the GI tract, process the images, and either store images on-board or transmit the images to external receiver. The capsule endoscope has to execute all the related tasks based on the power from one or more tiny batteries inside the capsule housing. Accordingly, the power is a very precious resource to operate the capsule endoscope. Therefore, it is desirable to squeeze out as much power from the batteries as possible. This is also true for many battery-powered electronic devices.

With the advancements in both semiconductors based on Moore's law for electronics with high speed complicated operation consuming low power, and battery technology to increase energy storage in smaller space, come the advent and then proliferation of battery powered devices, for example laptop computer and other handheld devices.

When battery becomes depleted, its internal resistance will increase and the voltage across its terminals will increase that will cause the output voltage to drop for the same current consumption. In this case, the circuits may malfunction. In this case, though the main function cannot be performed at the same speed, but it still can operate functions at a different (i.e., lower) speed or change to another function that can be performed with lower current consumption. In one embodiment, the same function can be performed but with a lower speed (e.x., ½ speed) and/or with a lower current. In another embodiment, another function with a lower current can be performed.

In another embodiment, the triggering event to switch to a lower speed or different function with a lower current is a power-on-reset. For example, a first function is performed for an amount of time T; if the power-on-reset is triggered, then the system switches to a lower speed or different lower current function. In another example, when the power voltage drop is over a certain threshold instead of a power-on-reset, the function change is triggered. The power voltage drop can be detected through some circuit functions.

Figure 3A:
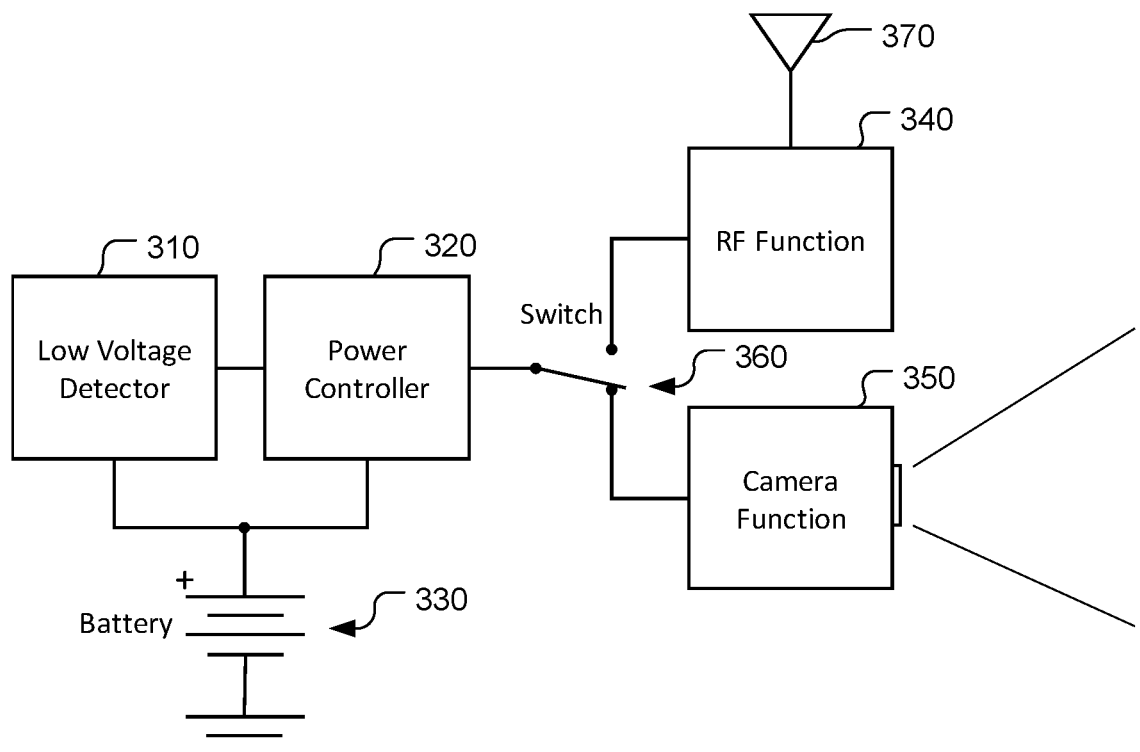
FIG. 3A illustrates an example of a capsule system having a power controller that switches on either the wireless function or the camera function.

FIG. 3A illustrates an example of a capsule endoscope that switches from one function and another function when a triggering event is detected. The capsule system having a power controller 320 that switches on (via. Switch 360) either the wireless function or RF function 340 or the camera function 350. A low voltage detector 310 is coupled to the battery 330 to detect the low battery event. The low voltage detector 310 can signal the power controller 320 when the low battery event is detected. An antenna 370 is coupled to the RF function 340 for transmit and/or receive.

In another embodiment, when the battery low event is triggered or detected, some functions are disabled and remaining functions can continue to be performed. In yet another embodiment, different functions are performed with a lower current such that the (peak current×battery internal resistance) is sufficiently low so that the functions are still operating. In yet another embodiment, some lower voltage functions continue to be performed or are activated to be performed since the IR drop (i.e., voltage drop) from the internal resistance does not affect the functions with such low-voltage operations. The lower voltage operation may be connected through a voltage regulator. In yet another embodiment, a switching regulator is used to cause less current drawn from the battery to further extend the operation time.

In one embodiment, a lower speed operation can be achieved by using a lower clock speed. In another embodiment, a lower speed operation is achieved through a lower VCC from a regulator output to cause the circuit to function slower, but to draw a less current. In yet another embodiment, the lower current is achieved by a lower analog circuit current setting, such as setting the biasing point with a lower transistor gate voltage, although it might affect the speed or quality.

In one embodiment, the system has a regulator connecting to the battery/batteries; switching to a lower speed may correspond to a lower voltage from the regulator output since the lower speed normally needs a lower VCC in order to further lower the current for the system to last even longer.

In another embodiment, when the switching occurs, the clock rate is lowered, or some modules in the system are shut down or disabled, or its clock is disabled. In another embodiment, a power switch is involved to turn off one function with a higher current and to turn on another function with a lower current. In another embodiment, the lower power function has lower VCC so that a different regular function is involved. With a switching regulator, this lower VCC regulator draws less current from the battery with the original voltage range.

Figure 3B:
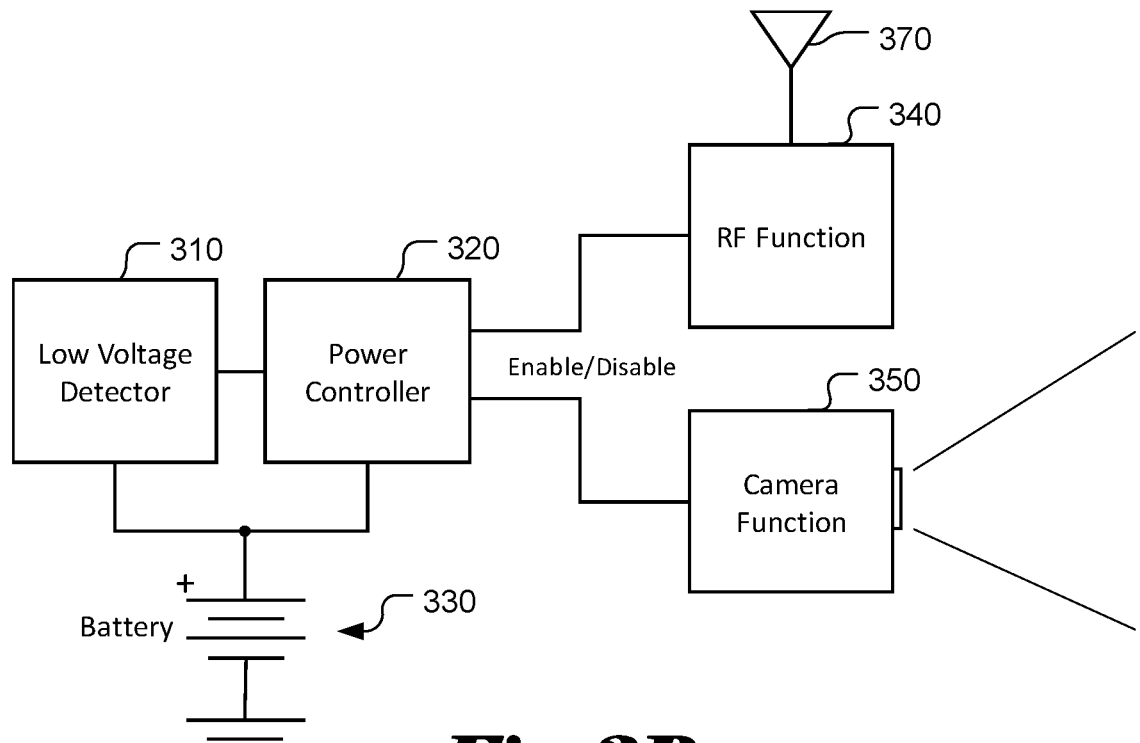
FIG. 3B illustrates an example of a capsule system having a power controller that enables/disables the wireless function or the camera function.

FIG. 3B illustrates an example of a capsule endoscope that uses the power controller 320 to enable/disable one of two functions (340 and 350) for switching from one function to another function when a triggering event is detected.

Figure 4:
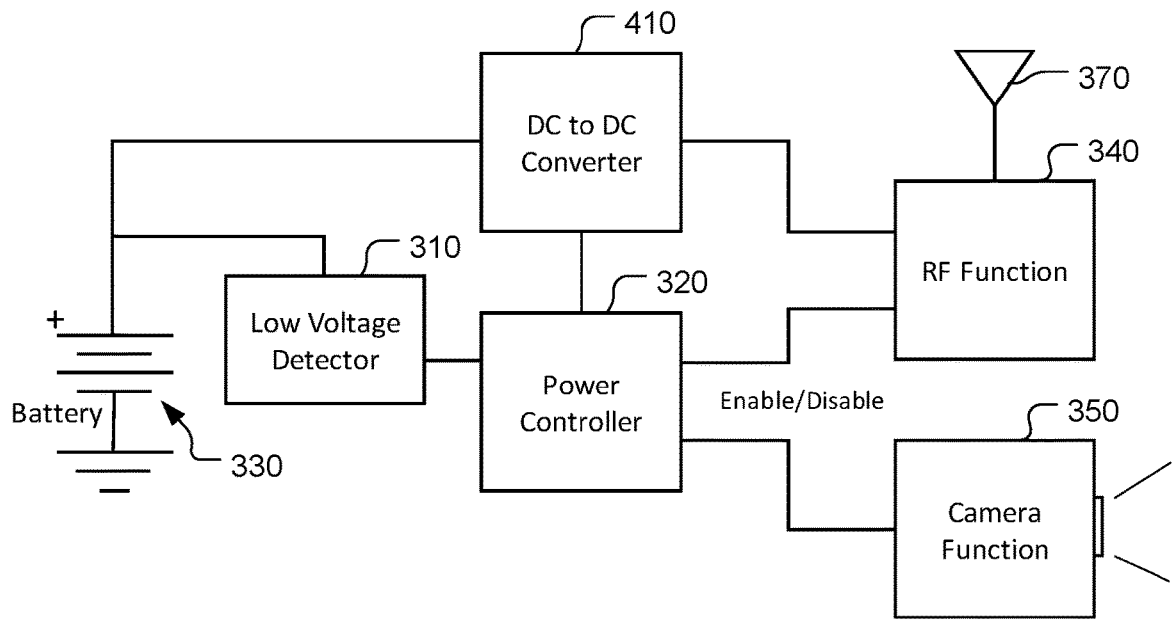
FIG. 4 illustrates an example of a capsule system having an efficient DC-to-DC converter that converts the power from high voltage to low voltage (e.g., 1 mA at 2.7V to ~2 mA at 1.3V). Once the low voltage condition is detected, the power convertor can disable the camera function and turn on the DC-to-DC converter and then enable the wireless function for the data transmit operation.

FIG. 4 illustrates an example of a capsule endoscope that uses the power controller 320 to enable/disable one of two functions (340 and 350) for switching from one function to another function when a triggering event is detected. Furthermore, the capsule endoscope includes a DC-to-DC converter 410 (i.e., a type of switching regulator) to provide a lower voltage for the RF function 340 to reduce the current. In FIGS. 3A, 3B, and 4, RF (i.e., wireless) and camera functions may have a common circuits module or circuits which are not explicitly shown in these figures. In FIG. 4, there might be circuits or modules with different VCC's communicating with each other.

When the larger than maximum allowable value of the (internal resistance×peak current) or below the lowest operation voltage of the battery output voltage is detected, disabling of certain function(s) to reduce the current must happen. However, certain other function(s) will only be enabled after a certain time or after a certain event or condition has occurred. For example, the condition corresponds to the detection of capsule excreted from the body.

An on-board storage capsule system could embody the above invention. While the device travels through the GI tract, the camera takes images and stored them in the on-board storage system. If the capsule is excreted in sufficiently short time, the normal imaging function (i.e., camera function) may still be in operation. The event of capsule exiting the human body can be detected. For example, the pixels of an image having substantial intensity with very low lighting or no lighting output (as measured by the current of the LED light source of the capsule) may indicate that the capsule has excreted from the body. This condition may trigger the capsule to switch from the imaging function to the wireless image transmission function to transmit on-board stored images and/or other data to an external device via a consumer band. The external device, for example, may be a specially designed wireless device or a mobile phone. In one embodiment, a temperature sensor can be included to work with the camera system to detect the excretion of the capsule and to initiate or switch to the wireless function in the capsule. In one embodiment, the special designed wireless device or mobile phone can further transmit the images to a PC or through the cloud, or LAN (Local Area Network), or other internet media to a destination.

If the capsule takes a long time to excrete and the battery may no longer be able to sustain the current due to the increased internal resistance. The power-on-reset function or other circuits, that are capable of detecting the battery or power bus voltage being too low, can be used to trigger the capsule system to switch into a wait or sleep mode of the wireless function. After wakeup, the capsule needs to operate at a lower current than the imaging function, or needs to operate at a lower voltage such that the desired function can be maintained even at the peak current. A temperature sensor can sense the change of the environment and switch the wireless function mode from wait to wake-up mode to transmit the images to a special designed wireless device or a consumer mobile device. After detecting the low battery energy, some camera functions may still operate to detect the capsule excretion. It may operate a low frame rate, without storing the images to avoid the need of high flash memory writing current, or only a subset of pixels from the sensor is used to detect the capsule excretion. In one embodiment the subset is formed by pixels substantially across the sensor array area for better detection of excretion. In one embodiment, the wireless function can be in the wait state to be waken up by the user.

In one embodiment, after the capsule has initially been turned on and operated in the camera function for a certain amount of time, T until the battery internal resistance increases to a certain level, the power-on-reset circuits or other circuits that are capable of detecting the battery or power bus voltage being too low can trigger the capsule system to switch from the camera function to the wireless function. The triggering point can be set based on the case requiring the peak operation current. Upon triggering, the system can be placed initially in a wait, sleep or wakeup mode, or initiate communication with an external device, such as a mobile phone. Alternatively, the wireless function can be turned on, whether in active communication state or in wait state to be waken up by an external device, at the excretion of the capsule. In one embodiment when the low voltage threshold at the peak current is detected, the camera enters a low-throughput monitor mode with low frame rate or a mode where only a subset of pixels are sensed with no light by the capsule LED's to detect the excretion of the capsule.

In another embodiment, a temperature sensor or other sensor can be used to cause the wireless function to change from the wait to the wake-up mode to start transmitting image data. A protocol can be executed between the capsule wireless system and the other wireless system, such as a smart phone or other wireless device, to establish the communication and enable the transfer of image data. In one embodiment, the switch from the camera function to the wireless function is through power switch (i.e., switching the power on/off for the circuits responsible for the camera function or the wireless function). In another embodiment, the wireless device may have a lower VCC requiring a different regulator. In another embodiment, this regulator is a switching regulator. In another embodiment, the wireless function is enabled from a disabled state.

In one embodiment, the wake-up circuit may use an event or a combination of events to detect the excretion of the capsule, or the detected excretion signal can be communicated to the capsule through another wireless device by the user, which is normally a patient. In another example, the wake-up circuit is disabled until the excretion of the capsule and the capsule can start to hear any signal from another wireless device. In yet another example, the capsule also can be the initiator of the wireless communication after the excretion is detected. In one embodiment, the duty cycle of the capsule to initiate the communication is small and the image transmission can start after handshake is made.

In another embodiment, after a certain camera operation time, T, the battery internal resistance increases to a level to trigger the power-on-reset or other circuits that are capable of detecting the battery or power bus voltage being too low, the camera function is disabled. A temperature sensor can be used to monitor the temperature change in the environment after excretion in order to initiate the wireless function.

In the above description, the concept of "wait for a period time, T" may increase reliability if the power system bounces. However, it may not be necessary, for example, especially when the system is robust in terms of contact bounce.

In the above discussion, when switching to a lower current mode, the lower current can be achieved by rescheduling the events within the function being performed by detaching the current consuming events so that the peak current causing the highest voltage drop through the battery resistance becomes lower.

All the switching methods mentioned above may be affected by the power-on-reset or some circuits detecting the voltage between VCC and GND being below a certain threshold. It also can be switched after a certain time TS, some accumulated results, such as the number of instructions executed, the number of images taken, the (total current×time) (i.e. charges) from the battery, the total power from the battery, the total number of pixels stored, or a combination thereof.

In one embodiment, after time TS or a number of images taken, or a combination thereof, the events may be scheduled differently so that one or more events are detached to reduce the peak current, which increases the total battery life or to increase the number of images taken. This may reduce the possible peak frame rate, Nevertheless, at the end of gastrointestinal tract, the capsule usually travels in a lower speed, which requires a lower frame rate for adequate examination. Also, the issue of prolonged operation time and the higher total number of images taken become a more important measure for complete study (i.e., the capsule still functioning when existing the gastrointestinal tract or reaching some anatomy that the procedure is considered complete).

In another embodiment, after time, TS or a number of images taken, or a combination thereof, the clock may be reduced. When the power-on-reset or other circuits that are capable of detecting the battery or power bus voltage being too low is triggered, the system is switched to sleep, wait state or wireless transmission. In the sleep or wait state, some events (e.g., detecting the capsule exiting form the human body) may trigger the wireless operation. In yet another embodiment, the switch into a next lower voltage current function may be put on hold to be executed after the detection of a certain event.

The wireless function sometimes can be trigger in vivo however. Since FCC requires in vivo medical device to operate at a medical implant band, and the capsule can be operated in a consumer band or another band different from the medical implant band once the capsule is excreted. In this embodiment, the wireless system has a dual band function and an antenna, and the antennas is capable of transmitting in dual band frequencies or two antenna are used, one for each band.

The logic mentioned above can be implemented using various programmable devices such as micro-controller, central processing unit (CPU), field programmable gate array (FPGA), digital signal processor (DSP), ASIC (Application Specific Integrated Circuit) or any programmable processor or circuitry.

The above description is presented to enable a person of ordinary skill in the art to practice the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

Figure 5:
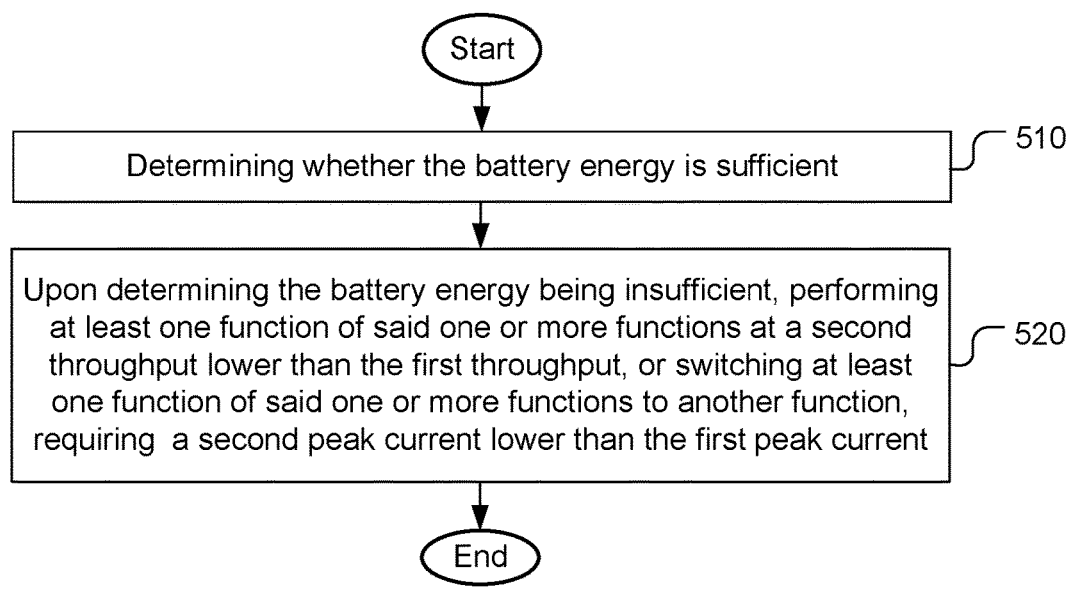
FIG. 5 illustrates an exemplary flowchart for a capsule endoscope incorporating an embodiment of the present invention.

FIG. 5 illustrates another exemplary flowchart for a capsule endoscope incorporating an embodiment of the present invention to leverage the battery residue energy, where one or more functions are performed by the capsule endoscope at a first throughput or a first peak current when the battery has sufficient energy. According to this method, whether the battery energy is sufficient is determined in step 510. Upon determining the battery energy being insufficient, at least one function of said one or more functions is performed at a second throughput lower than the first throughput, or at least one function of said one or more functions is switched to another function, requiring a second peak current lower than the first peak current in step 520.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of leveraging battery energy for a capsule endoscope powered by a battery, wherein one or more functions are performed by the capsule endoscope a first peak current when the battery has sufficient energy, the method comprising:
    determining whether the battery energy is sufficient; and
    upon determining the battery energy being insufficient switching at least one function of said one or more functions to another function, and wherein said another function requires a second peak current; and
    wherein the second peak current is such that (the second peak current×battery internal resistance) is sufficiently low, but said another functions is still operating.

2. The method of claim 1, wherein said determining whether the battery energy is sufficient corresponds to determining whether power-on reset is triggered, and wherein the battery energy is determined to be insufficient if said at least one function of said one or more functions has been performed for a period of time and the power-on reset is triggered.

3. The method of claim 1, wherein one or more low-voltage functions continue to operate or are activated to operate when the battery energy is insufficient, and wherein said one or more low-voltage functions are capable of operating at a lower voltage.

4. The method of claim 3, wherein a voltage regulator is used to provide the lower voltage.

5. The method of claim 4, wherein the voltage regulator corresponds to a switching regulator.

6. The method of claim 1, wherein the second peak current is achieved by lower analog circuit current setting for the capsule endoscope.

7. The method of claim 1, wherein said switching at least one function of said one or more functions to another function is achieved by using a power switch to turn off said at least one function of said one or more functions and to turn on said another function.

8. The method of claim 1 further comprises detecting whether the capsule endoscope has been excreted from a human body when the battery energy is still sufficient, and enabling a wireless function at a consumer band for the capsule endoscope to transmit images stored on-board to an external device upon detecting the capsule endoscope being excreted.

9. The method of claim 8, wherein said detecting whether the capsule endoscope has been excreted from the human body comprises detecting pixels of an image having substantial intensity with very low lighting or no lighting output from lighting sources of the capsule endoscope, and wherein the image is captured using a camera of the capsule endoscope.

10. The method of claim 9, wherein said detecting pixels of an image is based on a subset of pixels less than all pixels of camera sensor array of the capsule endoscope.

11. The method of claim 10, wherein the subset of pixels spreads across a substantial area of the camera sensor array of the capsule endoscope.

12. The method of claim 9, wherein a temperature is also used for aid detecting whether the capsule endoscope has been excreted from the human body.

13. The method of claim 8, wherein the external device corresponds to a specially designed wireless device or a mobile phone.

14. The method of claim 13, wherein the special designed wireless device or the mobile phone further transmits the images to a PC, or LAN (Local Area Network), or to a destination through a cloud network or other internet media.

15. A method of leveraging battery energy for a capsule endoscope powered by a battery, wherein one or more functions are performed by the capsule endoscope at a first peak current when the battery has sufficient energy, the method comprising:
determining whether the battery energy is sufficient; and
upon determining the battery energy being insufficient, switching at least one function of said one or more functions to another function, and wherein said another function requires a second peak current; and
wherein said switching at least one function of said one or more functions to another function corresponds to switching a camera function to a wireless function, and wherein the capsule endoscope is switched into a wait or sleep mode prior to the wireless function if the capsule endoscope has not been excreted from a human body.

16. The method of claim 15, wherein the capsule endoscope is waked up from the sleep mode and starts the wireless function upon detection of capsule excretion.

17. The method of claim 15, wherein when capsule excretion is detected, the wireless function is initiated either in active communication or by waken-up from a sleep mode by an external device.

18. The method of claim 17, wherein the camera function is disabled, or switched off, or partially working.

19. The method of claim 15, wherein the capsule endoscope is waken up from the sleep mode using a wake-up circuit, and wherein the wake-up circuit uses an event or a combination of events to detect excretion of the capsule endoscope and detected excretion signal is communicated to the capsule endoscope through another wireless device by a user.

20. A method of leveraging battery energy for a capsule endoscope powered by a battery, wherein one or more functions are performed by the capsule endoscope at a first peak current when the battery has sufficient energy, the method comprising:
determining whether the battery energy is sufficient; and
upon determining the battery energy being insufficient, switching at least one function of said one or more functions to another function, and wherein said another function requires a second peak current; and
wherein said switching at least one function of said one or more functions to another function corresponds to switching a camera function to an excretion detection function; and
wherein the excretion detection function is further switched to a wireless function to transmit images stored on-board upon capsule excretion detected.

21. A capsule endoscope, comprising:
a pixel array being responsive to light energy received by the pixel array;
one or more LED light sources to illuminate a scene for the pixel array;
one or more circuits coupled to the pixel array and the LED light source; and
a battery to supply electrical power to the pixel array, the LED light source and said one or more circuits;
an on-board memory to store images captured via the pixel array;
a wireless module with an antenna capable of transmitting the images stored on on-board memory; and
a housing adapted to be swallowed, wherein the battery, the pixel array, said one or more LED light sources, said one or more circuits, the on-board memory and the wireless module with the antenna are enclosed in the housing;
wherein said one or more circuits, the pixel array, said one or more LED light sources, the on-board memory and the wireless module with the antenna are capable of performing one or more functions at a first throughput or a first peak current when the battery has sufficient battery energy; and
wherein said one or more circuits, the pixel array and the LED light source are configured to:
determine whether the battery energy is sufficient; and
upon determining the battery energy being insufficient, switch at least one function of said one or more functions to another function, requiring a second peak current; and
wherein the second peak current is such that (the second peak current×battery internal resistance) is sufficiently low, but said another functions is still operating.

* * * * *